US008303634B2

(12) United States Patent  (10) Patent No.: US 8,303,634 B2
Martin                    (45) Date of Patent:     Nov. 6, 2012

(54) BONE SCREW, IN PARTICULAR FOR OSTEOSYNTHESIS

(75) Inventor: Jean-Jacques Martin, Bourg-En-Bresse (FR)

(73) Assignee: Small Bone Innovations International, Péronnas (FR)

( * ) Notice: Subject to any disclaimer, the term of this patent is extended or adjusted under 35 U.S.C. 154(b) by 927 days.

(21) Appl. No.: 12/129,258

(22) Filed: May 29, 2008

(65) Prior Publication Data

US 2008/0300639 A1 Dec. 4, 2008

(30) Foreign Application Priority Data

May 29, 2007 (FR) ...................................... 07 03783
May 21, 2008 (WO) ................... PCT/IB2008/051994

(51) Int. Cl.
*A61B 17/84* (2006.01)
*A61B 17/86* (2006.01)

(52) U.S. Cl. ........ 606/317; 606/315; 606/316; 411/412; 411/413

(58) Field of Classification Search .................. 606/275, 606/315–317; 411/378, 412–413
See application file for complete search history.

(56) References Cited

U.S. PATENT DOCUMENTS

| 4,463,753 | A |   | 8/1984 | Gustilo |         |
|-----------|---|---|--------|---------|---------|
| 5,387,212 | A | * | 2/1995 | Yuan et al. | 606/264 |
| 5,593,410 | A | * | 1/1997 | Vrespa  | 606/312 |
| 5,871,486 | A | * | 2/1999 | Huebner et al. | 606/305 |
| 6,030,162 | A |   | 2/2000 | Huebner |         |
| 6,053,916 | A |   | 4/2000 | Moore   |         |
| 2003/0028193 | A1 |   | 2/2003 | Weil et al. |   |
| 2003/0088251 | A1 | * | 5/2003 | Braun et al. | 606/73 |
| 2005/0038438 | A1 |   | 2/2005 | Anderson et al. | |
| 2005/0187552 | A1 |   | 8/2005 | Michelson |    |
| 2005/0261695 | A1 | * | 11/2005 | Cragg et al. | 606/86 |
| 2006/0189991 | A1 | * | 8/2006 | Bickley | 606/72 |

FOREIGN PATENT DOCUMENTS

EP  1273273 B1  9/2005
FR  2814937 A1  4/2002

(Continued)

*Primary Examiner* — Kevin T. Truong
*Assistant Examiner* — Larry E. Waggle, Jr.
(74) *Attorney, Agent, or Firm* — Morgan, Lewis & Bockius LLP

(57) ABSTRACT

A bone screw (1) having a threaded proximal portion (2), a threaded median portion (3), and a threaded distal portion (4). Threaded proximal portion (2) has a core (11) with a constant diameter and a proximal thread (12) with a constant diameter and a proximal pitch (P2). The threaded median portion (3) has a core (15), which is conical, with a diameter becoming increasingly larger from the distal end of the threaded median portion (3) to the proximal end thereof, and thread (16), which has a constant diameter smaller than the diameter of the thread (12) of the proximal threaded portion (2). The pitch of thread (16) of the threaded median portion (3) becomes increasingly smaller from the distal end of the threaded median portion (3) towards its proximal end. At the proximal end of the threaded median portion (3), the pitch of thread (16) is larger than the pitch (P2) of the thread (12) of the threaded proximal portion (2). The threaded distal portion (4) has a core (17) and thread (18), both having a constant diameter, and with thread (18) having a diameter that is smaller than the diameter of the thread (16). The pitch (P4) of the thread (18) of the threaded distal portion (4) is larger than the pitch of thread (16) at the distal end of the threaded median portion (3).

15 Claims, 3 Drawing Sheets

FOREIGN PATENT DOCUMENTS

| | | |
|---|---|---|
| FR | 2840799 A1 | 12/2003 |
| WO | 93/00518 A1 | 1/1993 |
| WO | 95/15727 A1 | 6/1995 |
| WO | 00/32125 A1 | 6/2000 |
| WO | 2004/069031 A2 | 8/2004 |
| WO | 2005/079685 A1 | 9/2005 |

\* cited by examiner

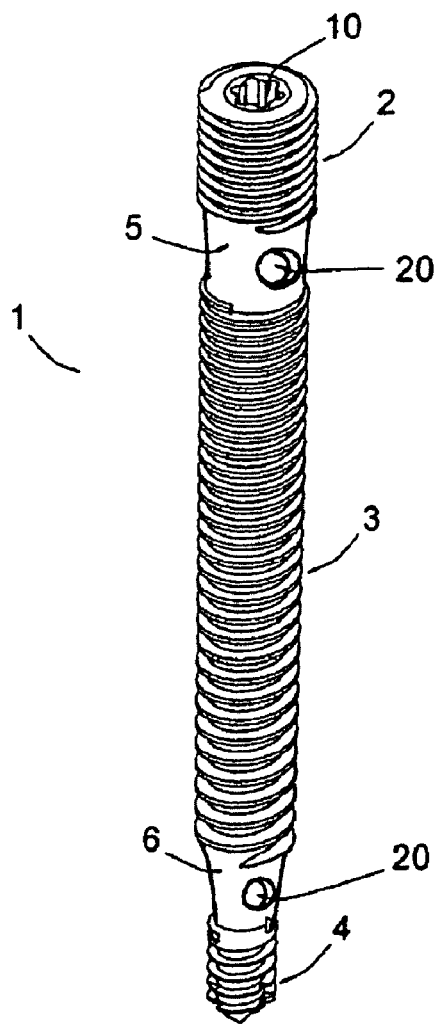
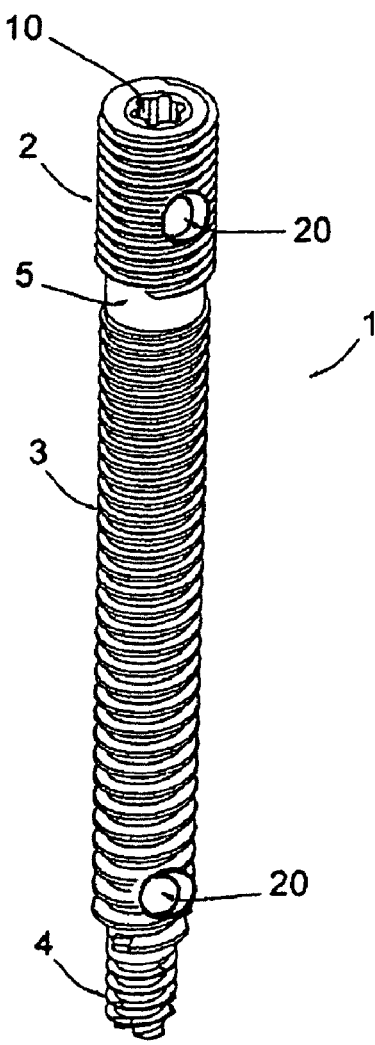
FIG. 6
FIG. 7

BONE SCREW, IN PARTICULAR FOR OSTEOSYNTHESIS

CROSS-REFERENCE TO RELATED APPLICATIONS

This application claims benefit of priority to French Patent Application No. 0703783, filed 29 May 2007 and currently pending, and International Patent Application No. PCT/IB2008/051994, filed 21 May 2008 and currently pending, both of which are incorporated herein by reference in their entirety.

FIELD OF THE INVENTION

This invention relates to a bone screw, in particular for osteosynthesis.

BACKGROUND OF THE INVENTION

Several types of bone screws are known, in particular for osteosynthesis, which combine two or more of the following characteristics:
1. with or without a head;
2. threaded over the entire length of the screw body or over only a portion of this body;
3. having a thread with a constant pitch or a larger pitch in the distal portion; in this second case, the screw enables the reduction of a fracture through which it is implanted, the rotation of the screw moving the distal bone fragment towards the proximal bone fragment, taking into consideration the difference in pitch; and
4. having a thread with a constant diameter or a diameter becoming increasingly larger from the distal end to the proximal end.

Existing screws do not give complete satisfaction as concerns carrying out an osteosynthesis, and this invention has the objective of remedying this disadvantage.

SUMMARY OF THE INVENTION

To that effect, the bone screw according to the invention includes:
(a) a threaded proximal portion, the core and thread of which have a constant diameter;
(b) a threaded median portion, the core of which is conical, having a diameter becoming increasingly larger from the distal end of this threaded median portion to the proximal end of this threaded median portion, and the thread of which has a constant diameter, smaller than the diameter of the thread of the proximal threaded portion; the pitch of the thread of this threaded median portion becomes increasingly smaller from said distal end towards said proximal end, and, at the proximal end of this threaded median portion, this pitch is larger than the pitch of the thread of the proximal threaded portion;
(c) a threaded distal portion, the core and the thread of which have a constant diameter and the thread of which has a diameter smaller than the diameter of the thread of the median threaded portion, the pitch of the thread of this threaded distal portion being larger than the pitch of the thread of the threaded median portion at the distal end of this threaded median portion.

In an embodiment of the invention, the bone screw has at least one transverse hole adapted to receive a screw or a pin to prevent rotation of the bone screw relative to a bone portion or fragment undergoing osteosynthesis. In another embodiment, the at least one transverse hole is a through hole. In another embodiment, the at least one transverse hole is not a through hole. In yet another embodiment the at least one transverse hole is smooth or tapped. In another embodiment, the at least one transverse hole is perpendicular to a longitudinal axis of the screw. In yet another embodiment, the at least one transverse hole is oblique in relation to a longitudinal axis of the screw.

In another embodiment, the bone screw includes at least two transverse holes, one of which is arranged in the threaded proximal portion and the other of which is arranged in the threaded distal portion.

In one embodiment of the invention, the screw includes at least one intermediate portion between the threaded distal portion and the threaded median portion and/or between the threaded median portion and the threaded proximal portion. In another embodiment, the at least one intermediate portion is flared. In yet another embodiment, the at least one intermediate portion is not flared. In another embodiment, the at least one intermediate portion is threaded. In yet another embodiment, the at least one intermediate portion is smooth.

In another embodiment, the screw includes at least one transverse hole arranged near the at least one intermediate portion.

The invention will be well understood, and other characteristics and advantages of it will become apparent, with reference to the appended schematic drawing, showing, for non-limiting illustrative purposes, several embodiments of the bone screw to which it relates.

BRIEF DESCRIPTION OF THE DRAWINGS

FIG. 6 illustrates a perspective view of a screw according to another embodiment of the present invention; and FIG. 7 illustrates a perspective view of a screw, according to yet another embodiment of the present invention.

DETAILED DESCRIPTION

For the sake of simplifying matters, the portions or elements of one embodiment which are found to be identical or similar in another embodiment will be identified by the same numeric references and will not be described again.

Figure 1:
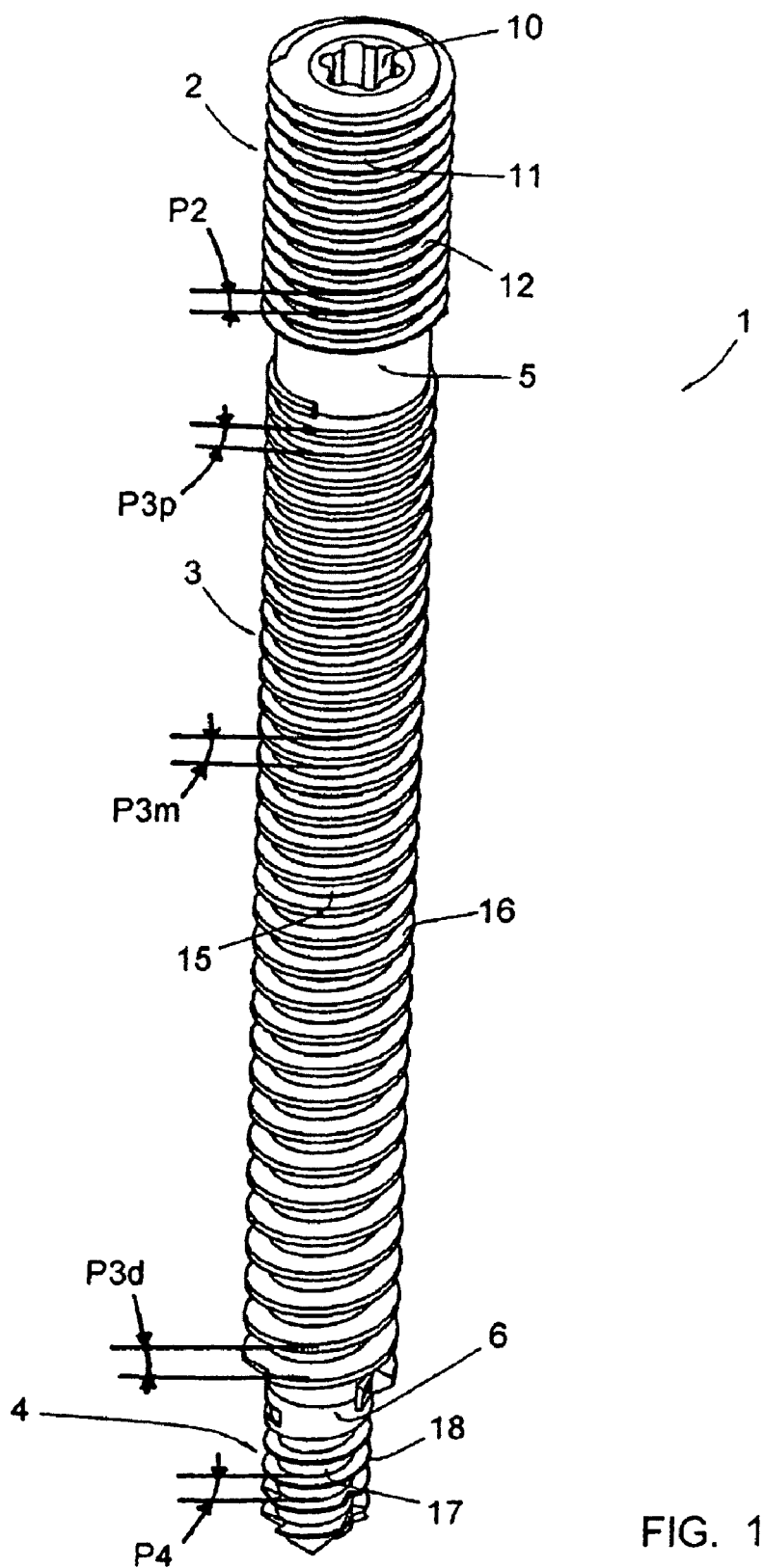
FIG. 1 illustrates a perspective view of a screw according to an embodiment of the present invention.

In the embodiment illustrated in FIG. 1, bone screw 1 has a threaded proximal portion 2, a threaded median portion 3 and a threaded distal portion 4, separated, respectively, by intermediate portions 5 and 6.

The threaded proximal portion 2 includes an axial cavity 10 for maneuvering the screw 1 in rotation and is threaded over its entire height. The core 11 and the thread 12 of the threaded proximal portion 2 have a constant diameter, and the pitch P2 of this thread 12 is constant.

The threaded median portion 3 is likewise threaded over its entire height. In one embodiment the core 15 of threaded median portion 3 is conical, having a diameter which decreases continuously from the distal end of this threaded median portion 3 towards the proximal end of the threaded median portion 3, and the thread 16 of the threaded median portion 3 has a constant diameter, smaller than the diameter of the thread 12 of portion 2. The pitch of the thread 16 decreases continuously and gradually from said distal end towards said proximal end. Consequently, threaded median portion 3 has a distal pitch $P3d$ that is larger than a median pitch $P3m$, itself being larger than the proximal pitch P3p. This proximal pitch P3p is larger than the pitch of the thread P2 of the threaded proximal portion 2.

In one embodiment the threaded distal portion 4 is likewise threaded over its entire height. The core 17 and the thread 18 of the threaded distal portion 4 have a constant diameter, and the pitch P4 of the thread 18 has a diameter smaller than the diameter of the thread 16 of the threaded median portion 3. The pitch P4 of threaded distal portion 4 is larger than the distal pitch P3d of portion 3 of the screw 1.

In one embodiment of the invention the intermediate portions 5 and 6 of screw 1 are cylindrical and smooth.

Figure 2:
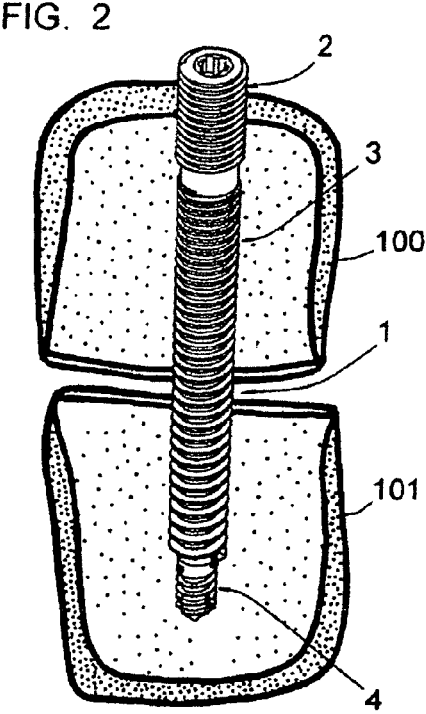
FIGS. 2 to 5 illustrate perspective views of the screw of FIG. 1 as it is being positioned in two bone fragments having to undergo osteosynthesis.
Figure 3:
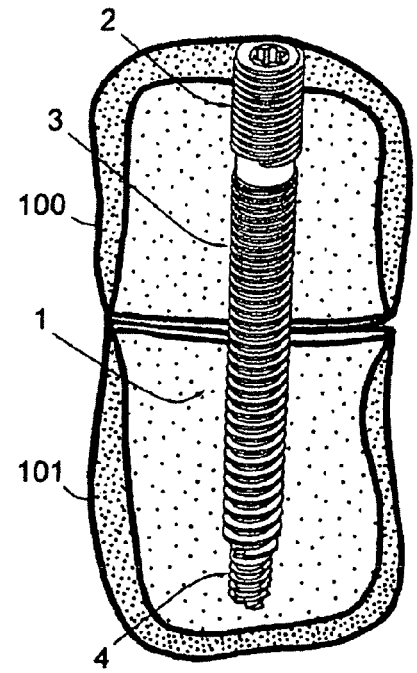

FIGS. 2 and 3 show the positioning of an embodiment of the screw 1 in two bone fragments 100 and 101, proximal and distal respectively, before and after reduction of the bone fracture by means of an embodiment of the screw 1. In bone fragments 100 and 101, illustrated in FIGS. 2 and 3, the cancellated bone and the subchondral bone are of good quality.

As illustrated in FIGS. 2 and 3, the embodiment of screw 1 is screwed into the proximal fragment 100 and then into the distal fragment 101 until the threaded portion 4 is supported in the subchondral bone and the threaded median portion 3 in the cancellated bone of the distal fragment 101. These supports operate securely, owing to the large pitches of the threaded distal portion 4 and of the distal portion of threaded median portion 3.

Referring to FIG. 3, continued screwing of an embodiment of screw 1 until insertion of the threaded proximal portion 2 thereof into the proximal cortical (see FIG. 3) makes it possible to carry out the reduction of the fracture separating the fragments 100 and 101, due to the gradual decrease in the pitch of the threaded median portion 3 in the proximal direction; this decrease leading to a more rapid advance of the screw 1 into the distal fragment 101 than into the proximal fragment 100, and therefore to a movement of this distal fragment 101 in relation to the proximal fragment 100.

Owing to the increase in the diameter of its core in the proximal direction, the threaded median portion 3 pushes the cancellated bone back radially and thereby produces a radial compaction of this cancellated bone and, owing to the gradual decrease in the pitch of its thread 16 of threaded median portion 3, produces an axial compression of this cancellated bone. This dual compression makes it possible to further strengthen the support of the screw 1 in the distal fragment 101 and to lightly compress the fragments 100 and 101, in order to perform the osteosynthesis under the best conditions; together with the insertion of the threaded proximal portion 2 into the cortical of the proximal fragment 100, it also ensures proper immobilisation of the screw 1 in rotation.

Figure 4:
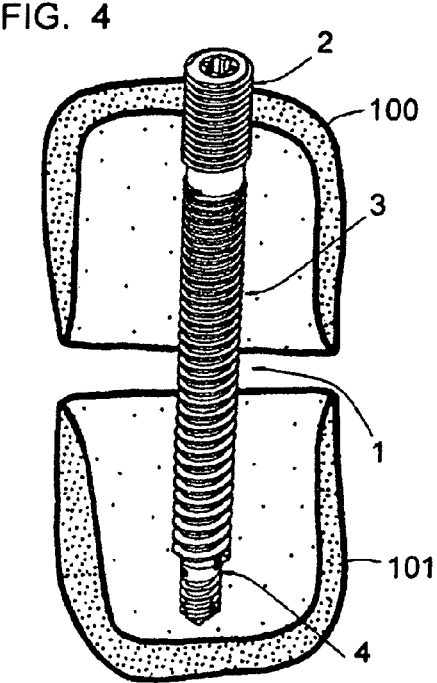
Figure 5:
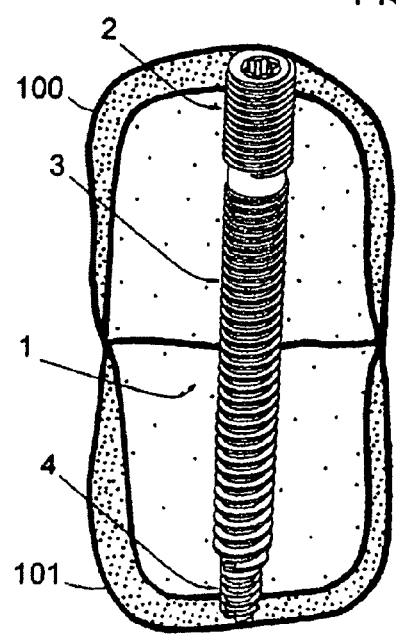

FIGS. 4 and 5 illustrate the case of two bone fragments 100, 101 in which the cancellated bone and the subchondral bone are depleted, or have even disappeared; positioning of the embodiment of screw 1 occurs in a similar manner, except that it is then necessary to insert the threaded distal portion 4 into the distal cortical.

Referring to FIGS. 4 and 5, during positioning of an embodiment of screw 1 through two bone portions or fragments, 100 and 101, having to undergo osteosynthesis, the threaded distal portion 4 is inserted into the distal cortical or subchondral bone of the distal fragment 101, the threaded median portion 3 intended to take position in the cancellated bone by gradually pushing this cancellated bone back radially, owing to the increase in the diameter of its core in the proximal direction, thereby compacting this cancellated bone, and the threaded proximal portion 2 of the screw 1 is inserted into the proximal cortical bone of the proximal fragment 100. The continuous decrease in the thread pitch of said threaded median portion 3 also enables axial compression of the cancellated bone.

FIG. 6 shows another embodiment of the screw 1, in which the intermediate portions 5 and 6 are drilled with smooth transverse holes 20, which pass straight through the screw 1, perpendicular to the longitudinal axis thereof. Each of these holes 20 is intended to receive a screw or a pin ensuring that the screw 1 is blocked in rotation in relation to the bone fragments 100, 101.

In an embodiment of the invention, screw 1 advantageously includes at least one transverse hole 20 intended to receive a screw or a pin ensuring that the screw is blocked in rotation in relation to a bone portion or fragment. In one embodiment, screw 1 is suited to ankle arthrodesis, as a replacement for an interlocking nail, enabling compression of the bone portions before locking is carried out.

Each transverse hole 20 can be a through-hole or not, smooth, or tapped, perpendicular to the longitudinal axis of screw 1 or oblique in relation to this axis.

In an embodiment of the invention, screw 1 preferably includes at least two transverse holes 20, one of which is arranged in the threaded proximal portion 2 of the screw 1 and the other arranged in the threaded distal portion of screw 1. Thus, one transverse hole 20 is intended to run near a proximal bone portion or bony fragment 100 and the other transverse hole 20 is intended to run near a distal portion or bony fragment 101, whereby screw 1 can be immobilised in rotation in relation to the two bony portions or fragments 100 and 101.

In an embodiment of the invention, screw 1 includes an intermediate portion 6 between the threaded distal portion 4 and the threaded median portion 3.

In another embodiment of the invention, screw 1 includes an intermediate portion 5 between the threaded median portion 3 and the threaded proximal portion 2.

In yet another embodiment of the invention, screw 1 includes an intermediate portion 6 between the threaded distal portion 4 and the threaded median portion 3 and an intermediate portion 5 between the threaded median portion 3 and the threaded proximal portion 2. Intermediate portions 5 and 6 can be flared or not, and/or threaded or smooth.

In an embodiment of the invention, transverse hole(s) 20 is (are) preferably arranged near said intermediate portion(s).

In the embodiment illustrated in FIG. 6, the distal intermediate portion 6 has a flared shape, ensuring a gradual transition between the proximal end of the threaded distal portion 4 and the distal end of the threaded median portion 3.

FIG. 7 shows yet another embodiment of the screw 1, in which the holes 20 are arranged through the threaded proximal portion 2 and through the distal portion of the threaded median portion 3. In this example, the screw 1 is devoid of any distal intermediate portion 6.

A bone screw 1 according to one embodiment of the invention includes a threaded proximal portion 2 and a threaded distal portion 4 with straight thread, suited to being perfectly supported in the cortical or subchondral bone, and a threaded median portion 3 of constant diameter but with a continuously increasing core diameter in the proximal direction; and with a continuously increasing thread height from the distal end towards the proximal end of the threaded median portion 3. In one embodiment, the pitch of the threads of the threaded distal portion 4, median portion 3 and proximal portion 2 decreases from the distal end of the screw towards the proximal end of the screw.

In one embodiment, the insertion of the threaded distal portion 4 into the subchondral or cortical bone and the radial and axial compaction of the cancellated bone around threaded median portion 3 enable screw 1 to be perfectly supported in the distal bone portion or fragment 101. Symmetrically, the threaded proximal portion 2 is inserted into the proximal cortical bone and enables threaded proximal portion 2 to be perfectly supported in the proximal bone portion or fragment 100. These perfect supports, combined with the decrease of the thread pitch from the distal end towards the proximal end of the screw, enable a reduction of the fracture to be achieved and the two bone portions or fragments to be held perfectly under light compression, and therefore osteosynthesis to be carried out under the best conditions, by simply inserting one or more screws according to the invention into these bone portions or fragments.

In one embodiment, when the subchondral bone is still of good quality, the thread of threaded median portion 3 itself alone enables sufficient support in the bony portions or fragments to bring them together and compress them; insertion of the threaded distal portion into the distal cortical bone is then not particularly necessary; conversely, when the subchondral bone is depleted, or even nonexistent, the support inside the distal bone portion or fragment is made by Inserting the threaded distal portion into the distal cortical bone.

As is apparent from the preceding, the invention provides a bone screw, for osteosynthesis in particular, which, in comparison with equivalent screws of the prior art, has the decisive advantage of enabling positioning in a bone, in particular for carrying out an osteosynthesis, under the best conditions, i.e., with a perfect hold on the bony fragments and the possibility of compressing these bony fragments, even in cases of cancellated or subchondral bones which are of poor quality or which have disappeared.

It stands to reason that the invention is not limited to the embodiment described above for illustrative purposes, but that it extends to all embodiments covered by the claims appended hereto.

The invention claimed is:

1. A bone screw (1) comprising
   (a) a threaded proximal portion (2) having
      a proximal core (11) with a constant diameter and
      a proximal thread (12) with a constant diameter and a proximal pitch;
   (b) a threaded median portion (3) having
      a conical median core (15) with a diameter that becomes increasingly larger from a distal end of the threaded median portion (3) to a proximal end of the threaded median portion (3) and
      a median thread (16) with a constant diameter which is smaller than the diameter of the proximal thread (12) and a median pitch that becomes increasingly smaller from the distal end of the threaded median portion (3) towards the proximal end of the threaded median portion (3), the median pitch at the proximal end of the threaded median portion (3) being larger than the proximal pitch; and
   (c) a threaded distal portion (4) having
      a distal core with a constant diameter (17) and
      a distal thread (18) with a constant diameter that is smaller than the diameter of the median thread (16) and a pitch that is larger than the pitch of the median thread (16) at the distal end of the threaded median portion (3).

2. The bone screw according to claim 1, further comprising at least one transverse hole (20) adapted to receive a screw or a pin to prevent rotation of the bone screw relative to a bone portion or fragment (100, 101).

3. The bone screw according to claim 2, wherein the at least one transverse hole (20) is a through hole.

4. The bone screw according to claim 2, wherein the at least one transverse hole (20) is not a through hole.

5. The bone screw according to claim 2, wherein the at least one transverse hole (20) is smooth.

6. The bone screw according to claim 2, wherein the at least one transverse hole (20) is tapped.

7. The bone screw according to claim 2, wherein the at least one transverse hole (20) is perpendicular to a longitudinal axis of the screw (1).

8. The bone screw according to claim 2, wherein the at least one transverse hole (20) is oblique in relation to a longitudinal axis of the screw (1).

9. The bone screw according to claim 2, wherein the bone screw includes at least two transverse holes (20), one of which is arranged in the threaded proximal portion and the other of which is arranged in the threaded distal portion.

10. The bone screw according to claim 1, further comprising at least one intermediate portion between the threaded distal portion (4) and the threaded median portion (3) or between the threaded median portion (3) and the threaded proximal portion (2) or between both.

11. The bone screw according to claim 10, wherein the at least one intermediate portion (5, 6) is flared.

12. The bone screw according to claim 10, wherein the at least one intermediate portion (5, 6) is not flared.

13. The bone screw according to claim 10, wherein the at least one intermediate portion is threaded.

14. The bone screw according to claim 10, wherein the at least one intermediate portion is smooth.

15. The bone screw according to claim 10, further comprising at least one transverse hole (20) arranged near the at least one intermediate portion.

* * * * *